(12) United States Patent
Goodall et al.

(10) Patent No.: US 6,441,260 B1
(45) Date of Patent: Aug. 27, 2002

(54) CATALYST AND PROCESS FOR PREPARING OLIGOMERS OF α-METHYLSTYRENE

(75) Inventors: Brian Leslie Goodall, Baton Rouge, LA (US); Brian Michael King, Kingsport, TN (US)

(73) Assignee: The B.F. Goodrich Company, Brecksville, OH (US)

( * ) Notice: Subject to any disclaimer, the term of this patent is extended or adjusted under 35 U.S.C. 154(b) by 0 days.

(21) Appl. No.: 09/585,062

(22) Filed: Jun. 1, 2000

Related U.S. Application Data

(60) Provisional application No. 60/137,617, filed on Jun. 4, 1999.

(51) Int. Cl.[7] .................................................. C07C 2/72
(52) U.S. Cl. ....................................................... 585/428
(58) Field of Search .......................................... 585/428

(56) References Cited

U.S. PATENT DOCUMENTS 4,414,370 A  * 11/1983  Hamielec et al. ............. 526/88

FOREIGN PATENT DOCUMENTS

| WO | 95/29940 | * 11/1995 |
| WO | 9633147  | 10/1996 |

* cited by examiner

*Primary Examiner*—Thuan D. Dang
(74) *Attorney, Agent, or Firm*—Thoburn T. Dunlap; Hudak & Shunk Co., LPA

(57) ABSTRACT

Low molecular weight α-methylstyrene oligomers are obtained by oligomerizing α-methylstyrene in the presence of a single component initiator complex containing a cation component and a weakly coordinating anion component. The initiator complex is non-corrosive and does not have to be neutralized or removed from the obtained product.

27 Claims, No Drawings

CATALYST AND PROCESS FOR PREPARING OLIGOMERS OF α-METHYLSTYRENE

This application claims benefit of provisional application No. 60/137,617, filing date Jun. 4, 1999.

BACKGROUND OF THE INVENTION

1. Technical Field

The present invention relates to a process for oligomerizing alpha-methylstyrene and an initiator therefor. More particularly, the invention is directed to preparing oligomers of alpha-methylstyrene having a number-average molecular weight ($M_n$) of about 5,000 and below.

2. Background

Alpha-methylstyrene (α-methylstyrene) has been utilized as a monomer and comonomer in many polymerization processes. The polymerization products of such processes have been put to use as adjuvants in polymeric compositions, improving the impact and heat-resistant properties of polymers. When admixed with polyvinyl chloride (PVC) low molecular weight poly(α-methylstyrene) reduces the fusion time and melt viscosity of the PVC composition and improves its heat stability. Low molecular weight α-methylstyrene oligomers also improve the melt fracture and shear burning resistance of PVC at high shear processing rates (Wilson A. P.; Raimondi, V. V.; Polym. Eng. Sci. (1978). 18(11), 887–92).

Oligomers of α-methylstyrene have also been employed as processing aids for chlorinated polyvinyl chloride (CPVC). Incorporation of poly(α-methylstyrene) into CPVC reduces fusion time and melt viscosity and improves fusion, melt flow, and stability, without deleteriously affecting the desirable properties of the polymer composition (Raimondi, V.; Wilson, Alfred P.; Soc. Plast. Eng. Tech. Pap. (1978), 24, 747–9).

Heretofore, low molecular weight poly(α-methylstyrene) has been produced by polymerizing α-methylstyrene in the presence of Lewis acid initiators such as $BF_3$, $BCl_3$, and $SbCl_5$ in combination with an aluminum halides and the like. In commercial practice, low molecular weight poly(α-methylstyrene) has been provided by polymerizing α-methylstyrene in the presence of a $BF_3$/water mixture. However, such catalyst systems have been demonstrated to be highly corrosive, resulting in many engineering problems leading to eventual shut down of the manufacturing plant. The corrosive nature of the $BF_3$/water and aluminum halide mixtures have necessitated the use of expensive metal alloys in manufacturing plant design. Even when such measures have been employed, the corrosive nature of the residual catalyst system dictated that the spent catalyst system had to be neutralized and removed from the obtained product. What is desired is an oligomerization process involving mild reaction conditions and a simple initiator system.

SUMMARY OF THE INVENTION

Accordingly, it is a general object of the present invention to provide a process for the oligomerization of α-methylstyrene.

It is another object of the invention to provide a process for α-methylstyrene oligomerization utilizing inert reaction media.

It is yet another object of the invention to provide an initiator system that does not need to be neutralized or removed from the oligomerized product.

It is still another object of the invention to provide a poly(α-methylstyrene) product having a number average molecular weight of about 5000 and below.

It is another object of the invention to provide an oligomerized α-methylstyrene product having a number average molecular weight of about 500 to 5000.

In accordance with the present invention, it has been discovered that α-methylstyrene can be oligomerized when contacted with a catalytic amount of a single component initiator comprising a cation and a weakly coordinating anion (WCA) at a temperature ranging from about −15° C. to about 40° C. By weakly coordinating anion is meant that the anion is only weakly coordinated to the cation complex. The anion is sufficiently labile to be displaced by monomer. The WCA functions as a stabilizing anion to the cation complex and does not transfer to the cation complex to form a neutral product. The WCA is relatively inert in that it is non-oxidative, non-reducing, and non-nucleophilic.

The cation portion of the single component initiator useful in the process of the invention is selected from lithium or a carbocation of the formula:

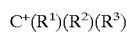

wherein $R^1$, $R^2$, and $R^3$, independently represent hydrocarbyl and substituted hydrocarbyl radicals.

The WCA portion of the single component initiator useful in the process of the present invention is selected from a borate of the formula:

wherein $R^4$, independently represents a fluorinated aryl radical and $R^5$ represents a radical selected from hydrocarbyl, fluorinated hydrocarbyl or fluorinated aryl.

International Published Patent Application No. WO 95/29940 discloses a cationic catalyst system for polymerizing olefinic and styrenic monomers to high polymers having molecular weights above 10,000 $M_n$, and most preferably above 100,000 $M_n$. The catalyst system includes a cationic component selected from a hydrocarbyl substituted carbocation or a cyclopentadienyl transition metal cations and a non-coordinating anionic complex including hydrocarbyl substituted borates. The catalyst system is combined with the monomer in slurry or solution and the polymerization reaction is conducted at temperatures below about 20° C., and more preferably between −150 and −20°. There is no disclosure of a process for making oligomers of α-methylstyrene.

T. D. Shaffer and J. R. Ashbaugh, J. Poly. Sci., Part A, Vol. 35, 329–344 (1997) (Table IX), have reported polymerizing (α-methylstyrene) to a $M_n$ of 6400 in the presence of a multicomponent catalyst system consisting of lithium n-butyltrispentafluorophenylboron and the initiator 1,3-bis (1-chloro-1-methylethyl)-5-tert-butylbenzene. However, there is no disclosure of a single component catalyst system capable of producing poly(α-methylstyrene) oligomers having molecular weights of 5000 or below ($M_n$)

DETAILED DESCRIPTION

The present invention is directed to a non-corrosive initiator system and process for oligomerizing (α-methylstyrene) to low molecular weight poly(α-methylstyrene). By low molecular weight is meant that the α-methylstyrene oligomer has a number average molecular weight ($M_n$) of 5000 and below (relative to a polystyrene standard). In one aspect of the invention the molecular weight of the oligomerized α-methylstyrene ranges between 500 and 4500 $M_n$. In another aspect of the invention the molecular weight of the oligomerized α-methylstyrene ranges between 1000 and 4000 $M_n$. The desired oligomers are made in inert (non-corrosive) media in the absence of water and the corrosive compounds of the prior art, obviating the need for the use of expensive alloys in the physical plant and by-passing the necessity to neutralize and remove catalyst components from the resulting product.

In one embodiment of the invention the polydispersity (Mw/Mn) is 10 or less. In another embodiment the polydispersity is 5 or less. In still another embodiment it ranges from 1.5 to 4, and in another embodiment it ranges from 2 to 3.5.

The single component catalyst system of the invention is represented by the formula:

In the formula above, M represents lithium or a carbocation of the formula:

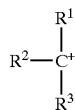

wherein $R^1$, $R^2$, and $R^3$, independently represent hydrocarbyl and substituted hydrocarbyl radicals. In one aspect of the invention, the hydrocarbyl and substituted hydrocarbyl radicals are independently selected from hydrogen, linear or branched ($C_1$ to $C_{20}$) alkyl, ($C_5$ to $C_{10}$) cycloalkyl, ($C_6$ to $C_{14}$) aryl, and ($C_7$ to $C_{24}$) aralkyl, provided that only one of $R^1$, $R^2$, and $R^3$ can be hydrogen at any one time. By substituted is meant that the hydrocarbyl radical can be substituted with a halide selected from chlorine, fluorine, bromine, and iodine, or with another hydrocarbyl group selected from ($C_1$ to $C_{10}$) alkyl, ($C_5$ to $C_{10}$) cycloalkyl, ($C_6$ to $C_{14}$) aryl, and ($C_7$ to $C_{24}$) aralkyl. In another aspect, the carbocations of the invention contain aryl radicals wherein $R^1$, $R^2$, and $R^3$ are selected from phenyl, tolyl, xylyl, and biphenyl. In still another aspect, the carbocation is selected from triphenylcarbenium or trityl.

The WCA component of the initiator complex represented in the above formula is a boron containing compound of the formula:

wherein $R^4$ independently represents a substituted ($C_6$ to $C_{14}$) aryl radical and wherein two or more of the available valences on the aryl radical are substituted by fluorine, linear and branched ($C_1$ to $C_{20}$) fluoroalkyl, fluorophenyl and combinations thereof. Other substituents on the substituted aryl radical can include linear and branched ($C_1$ to $C_{10}$) alkyl, linear or branched ($C_2$ to $C_{20}$) alkenyl, ($C_5$ to $C_{10}$) cycloalkyl, ($C_6$ to $C_{14}$) aryl, and ($C_7$ to $C_{24}$) aralkyl. By fluoroalkyl is meant that at least one hydrogen atom on the alkyl radical is replaced by a fluorine atom. By fluorophenyl is meant that at least one hydrogen atom on the phenyl radical is replaced by a fluorine atom. The degree of fluorination of the fluoroalkyl and fluorophenyl groups can range from one hydrogen atom on the alkyl and phenyl groups being replaced by a fluorine atom (e.g., monofluoromethyl, monofluorophenyl) to full fluorination (perfluorination) wherein all available hydrogen atoms on the alkyl and phenyl groups have been replaced with fluorine atoms (e.g., trifluoromethyl (perfluoromethyl), and pentafluorophenyl (perfluorophenyl)). $R^5$ represents $R^4$ as defined above or a hydrocarbyl radical including hydrogen, linear or branched ($C_1$ to $C_{20}$) alkyl, linear or branched ($C_2$ to $C_{20}$) alkenyl, ($C_5$ to $C_{10}$) cycloalkyl, ($C_6$ to $C_{14}$) aryl, and ($C_7$ to $C_{24}$) aralkyl.

Representative borate anions include tetrakis(pentafluorophenyl)borate, tetrakis(3,5-bis(trifluoromethyl)phenylborate, tetrakis(3,5-difluorophenyl)borate, tetrakis(2,3,4,5-tetrafluorophenyl)borate, tetrakis(3,4,5,6-tetrafluorophenyl)borate, tetrakis(3,4,5-trifluorophenyl)borate, methyltris(perfluorophenyl)borate, ethyltris(perfluorophenyl)borate, phenyltris(perfluorophenyl)borate, and tetrakis(perfluorobiphenyl)borate.

Suitable initiators of the invention include lithium tetrakis(perfluorophenyl)borate and trityl tetrakis(perfluorophenyl)borate.

The initiators of the present invention can be combined with the (α-methylstyrene) monomer as a pre-formed single component initiator of the formula:

wherein M and WCA are as previously defined or they can be formed by combining the cation and anion precursor compounds in monomer wherein the active initiator is formed in situ.

In one aspect of the invention, the ratio of monomer to initiator employed in the present process can range from between about 2000:1 to about 1,000,000:1 (mole:mole basis). In another aspect, the ratio of monomer to initiator can range from about 10,000:1 to about 20,000:1 (mole:mole basis).

The process comprises contacting α-methylstyrene with a catalytic amount of the initiator defined above at a temperature range of about −15° C. to about 35° C. In another aspect the reaction temperature can range from about 0° C. to 30° C., and in a further aspect between 5° C. and 25° C. Surprisingly, it has been discovered that the molecular weight of the α-methylstyrene oligomer can be kept consistently below about 5000 $M_n$ by running the reaction at a temperature between −15° C. and 35° C.

The reaction can be conducted in bulk, slurry, or in solution. Suitable diluents include hydrocarbons and aromatic hydrocarbons. Suitable hydrocarbon diluents can be selected from linear and branched $C_3$ to $C_6$ alkanes such as propane, butane, pentane, hexane and cyclohexane. Suitable aromatic diluents include benzene, toluene, xylenes, and cumene.

The hydrocarbon diluents are non-solvents for the oligomeric product. Accordingly, the α-methylstyrene oligomeric product will precipitate from solution following the reaction, allowing for the easy recovery of the product via conventional separation means such as filtration. When the oligomerization reaction is conducted in an aromatic diluent, the product is a cement comprising the α-methylstyrene oligomer and diluent. The diluent can be removed by extruding the cement composition on a conventional devolatizing extruder.

In solution, the weight percent of monomer in diluent preferably ranges from 10 to 80 percent, more preferably 20 to 70 percent, and more preferably 30 to 60 percent.

The oligomers produced in accordance with this invention can be used for many purposes well known in the art, for example, as chemical intermediates, and as processing and heat stability aids for PVC and CPVC.

The following examples are presented solely for illustrative purposes and serve to exemplify various aspects of the

EXAMPLE 1

To a septum sealed 20 ml glass serum bottle, equipped with a magnetic stir bar was added degassed α-methylstyrene (5.15 g, 43.6 mmol) containing 3.2 ppm water. The concentration of water in the monomer was determined by Karl-Fisher coulombic titration. Thereafter, was added lithium tetrakis(pentafluorophenyl)borate (14.6 mg, 21.2 µmol) dissolved in dichloroethane (1.0 ml). The resulting solution was stirred at 22° C. and the bulk reaction proceeded for 45 minutes. The resulting polymer was dissolved in toluene (15 ml) and isolated by pouring the toluene solution into rapidly stirring methanol (350 ml). The fine white powder was then filtered and washed with excess methanol prior to drying to constant weight under vacuum at 60° C.

The dried, white α-methylstyrene polymer was found to weigh 3.18 g. The molecular weight (relative to polystyrene standards) was measured using GPC methods and found to be: $M_w$ 4,800, $M_n$ 1,700 and polydispersity 2.91.

EXAMPLE 2

To a septum sealed 20 ml glass serum bottle, equipped with a magnetic stir bar was added degassed (α-methylstyrene (5.07 g, 42.9 mmol) containing 3.2 ppm water. The concentration of water in the monomer was determined by Karl-Fisher coulombic titration. Thereafter, was added lithium tetrakis(pentafluorophenyl)borate (3.1 mg, 4.5 µmol) dissolved in dichloroethane (1.0 ml). The resulting solution was stirred at 22° C. and the bulk reaction proceeded for 120 minutes. The resulting polymer was dissolved in toluene (15 ml) and isolated by pouring the toluene solution into rapidly stirring methanol (350 ml). The fine white powder was then filtered and washed with excess methanol prior to drying to constant weight under vacuum at 60° C.

The dried, white (α-methylstyrene polymer was found to weigh 3.38 g. The molecular weight (relative to polystyrene standards) was measured using GPC methods and found to be: $M_w$ 7,800, $M_n$ 3,000 and polydispersity 2.58.

EXAMPLE 3

To a septum sealed 20 ml glass serum bottle, equipped with a magnetic stir bar was added degassed α-methylstyrene (5.08 g, 43.0 mmol) containing 3.2 ppm water. The concentration of water in the monomer was determined by Karl-Fisher coulombic titration. Thereafter, was added lithium tetrakis(pentafluorophenyl)borate (1.8 mg, 2.6 µmol) dissolved in dichloroethane (1.0 ml). The resulting solution was stirred at 22° C. and the bulk reaction proceeded for a total of 62 hours. The resulting polymer was dissolved in toluene (15 ml) and isolated by pouring the toluene solution into rapidly stirring methanol (350 ml). The fine white powder was then filtered and washed with excess methanol prior to drying to constant weight under vacuum at 60° C.

The dried, white α-methylstyrene polymer was found to weigh 3.83 g. The molecular weight (relative to polystyrene standards) was measured using GPC methods and found to be: $M_w$ 8,500, M2,600 and polydispersity 3.22.

EXAMPLE 4

To a septum sealed 20 ml glass serum bottle, equipped with a magnetic stir bar was added degassed α-methylstyrene (11.15 g, 94.3 mmol) containing 8.7 ppm water. The concentration of water in the monomer was determined by Karl-Fisher coulombic titration. The bottle containing monomer was then immersed in an ice water bath at 0° C. prior to addition of initiator. Thereafter, was added triphenylmethyl tetrakis(pentafluorophenyl)borate (0.8 mg, 0.87 µmol) dissolved in dichloroethane (1.0 ml). The resulting solution was stirred in an ice water bath maintained at 0° C. and the bulk reaction proceeded for a total of 10 minutes. The resulting polymer was dissolved in tetrahydrofuran (15 ml) and isolated by pouring the tetrahydrofuran solution into rapidly stirring methanol (350 ml). The fine white powder was then filtered and washed with excess methanol prior to drying to constant weight under vacuum at 60° C.

The dried, white α-methylstyrene polymer was found to weigh 5.95 g. The molecular weight (relative to polystyrene standards) was measured using GPC methods and found to be: $M_w$ 8,200, $M_n$ 2,500 and polydispersity 3.21.

EXAMPLE 5

To a septum sealed 50 ml glass serum bottle, equipped with a magnetic stir bar were added degassed α-methylstyrene (11.05 g, 93.5 mmol) containing 8.7 ppm water and dry toluene (11.09 g). The concentration of water in the monomer was determined by Karl-Fisher coulombic titration. The bottle containing the monomer solution (50% AMS in toluene) was then immersed in an ice water bath at 0° C. prior to addition of initiator. Thereafter, was added triphenylmethyl tetrakis(pentafluorophenyl)borate (0.5 mg, 0.54 µmol) dissolved in dichloroethane (1.0 ml). The resulting solution was stirred in an ice water bath maintained at 0° C. for a total of 10 minutes. The resulting polymer was isolated by pouring the toluene solution into rapidly stirring methanol (350 ml). The fine white powder was then filtered and washed with excess methanol prior to drying to constant weight under vacuum at 60° C.

The dried, white α-methylstyrene polymer was found to weigh 4.74 g. The molecular weight (relative to polystyrene standards) was measured using GPC methods and found to be: $M_w$ 10,500, $M_n$ 2,900 and polydispersity 3.69.

EXAMPLE 6

To a septum sealed 20 ml glass serum bottle, equipped with a magnetic stir bar was added degassed α-methylstyrene (4.79 g, 40.5 mmol) containing 5.7 ppm water. The concentration of water in the monomer was determined by Karl-Fisher coulombic titration. Thereafter, was added lithium tetrakis(pentafluorophenyl)borate (2.8 mg, 4.1 µmol) dissolved in dichloroethane (0.5 ml). The resulting solution was stirred at 22° C. until stirring had become labored. The resulting polymer was dissolved in tetrahydrofuran (15 ml) and isolated by pouring the tetrahydrofuran solution into rapidly stirring methanol (350 ml). The fine white powder was then filtered and washed with excess methanol prior to drying to constant weight under vacuum at 60° C.

The dried, white α-methylstyrene polymer was found to weigh 3.42 g. The molecular weight (relative to polystyrene standards) was measured using GPC methods and found to be: $M_w$ 9,700, $M_n$ 3,300 and polydispersity 2.99.

EXAMPLE 7

To a septum sealed 50 ml glass serum bottle, equipped with a magnetic stir bar was added degassed α-methylstyrene (11.05 g, 9.35 mmol) containing 5.7 ppm water. The concentration of water in the monomer was determined by Karl-Fisher coulombic titration. The bottle containing monomer was then immersed in an ice water bath at 0° C. prior to addition of initiator. Thereafter, was added triphenylmethyl tetrakis(pentafluorophenyl)borate (0.5 mg, 0.54 μmol) dissolved in dichloroethane (0.5 ml). The resulting solution was stirred in an ice water bath maintained at 0° C. and the bulk reaction proceeded for a total of 10 minutes. The resulting polymer was dissolved in tetrahydrofuran (15 ml) and was isolated by pouring the toluene solution into rapidly stirring methanol (350 ml). The fine white powder was then filtered and washed with excess methanol prior to drying to constant weight under vacuum at 60° C.

The dried, white α-methylstyrene polymer was found to weigh 1.00 g. The molecular weight (relative to polystyrene standards) was measured using GPC methods and found to be: $M_w$ 6,400, $M_n$ 2,000 and polydispersity 3.28.

EXAMPLE 8

To a septum sealed 20 ml glass serum bottle, equipped with a magnetic stir bar was added degassed α-methylstyrene (4.94 g, 41.8 mmol) containing 4.5 ppm water. The concentration of water in the monomer was determined by Karl-Fisher coulombic titration. Thereafter, was added lithium tetrakis(pentafluorophenyl)borate (14.2 mg, 20.7 μmol) dissolved in dichloroethane (0.5 ml). The resulting solution was stirred at 22° C. and the bulk reaction proceeded for 60 minutes. The resulting polymer was dissolved in toluene (10 ml) and isolated by pouring the toluene solution into rapidly stirring methanol (350 ml). The fine white powder was then filtered and washed with excess methanol prior to drying to constant weight under vacuum at 60° C.

The dried, white α-methylstyrene polymer was found to weigh 2.64 g. The molecular weight (relative to polystyrene standards) was measured using GPC methods and found to be: $M_w$ 3,800, $M_n$ 921 and polydispersity 4.08.

EXAMPLE 9

To a septum sealed 50 ml glass serum bottle, equipped with a magnetic stir bar was added degassed α-methylstyrene (10.16 g, 86.0 mmol) containing 4.5 ppm water. The concentration of water in the monomer was determined by Karl-Fisher coulombic titration. The bottle containing monomer was then immersed in an ice water bath at 0° C. prior to addition of initiator. Thereafter, was added triphenylmethyl tetrakis(pentafluorophenyl)borate (0.9 mg, 0.98 μmol) dissolved in dichloroethane (0.5 ml). The resulting solution was stirred in an ice water bath maintained at 0° C. and the bulk reaction proceeded for a total of 30 minutes. The resulting polymer was dissolved in tetrahydrofuran (20 ml) and was isolated by pouring the toluene solution into rapidly stirring methanol (350 ml). The fine white powder was then filtered and washed with excess methanol prior to drying to constant weight under vacuum at 60° C.

The dried, white α-methylstyrene polymer was found to weigh 7.58 g. The molecular weight (relative to polystyrene standards) was measured using GPC methods and found to be: $M_w$ 2,200, $M_n$ 900 and polydispersity 2.44.

EXAMPLE 10

To a septum sealed 50 ml glass serum bottle, equipped with a magnetic stir bar was added degassed α-methylstyrene (10.67 g, 90.3 mmol) containing 4.5 ppm water. The concentration of water in the monomer was determined by Karl-Fisher coulombic titration. The bottle containing monomer was then immersed in an ice water bath at 0° C. prior to addition of initiator. Thereafter, was added triphenylmethyl tetrakis(pentafluorophenyl)borate (0.9 mg, 0.98 μmol) dissolved in dichloroethane (0.5 ml). The resulting solution was stirred in an ice water bath maintained at 0° C. and the bulk reaction proceeded for a total of 30 minutes. The resulting polymer was dissolved in tetrahydrofuran (20 ml) and was isolated by pouring the toluene solution into rapidly stirring methanol (350 ml). The fine white powder was then filtered and washed with excess methanol prior to drying to constant weight under vacuum at 60° C.

The dried, white α-methylstyrene polymer was found to weigh 6.60 g. The molecular weight (relative to polystyrene standards) was measured using GPC methods and found to be: $M_w$ 2,400, $M_n$ 960 and polydispersity 2.47.

EXAMPLE 11

To a septum sealed 50 ml glass serum bottle, equipped with a magnetic stir bar were added degassed α-methylstyrene (15.02 g, 127 mmol) containing 11.6 ppm water and dry toluene (8.07 g). The concentration of water in the monomer was determined by Karl-Fisher coulombic titration. The bottle containing the monomer solution (70% wt. AMS in toluene) was then immersed in an ice water bath at 0° C. prior to addition of initiator. Thereafter, was added triphenylmethyl tetrakis (pentafluorophenyl)borate (1.3 mg, 1.4 μmol) dissolved in dichloroethane (0.5 ml). The resulting solution was stirred in an ice water bath maintained at 0° C. for a total of 60 minutes. The resulting polymer solution was diluted with tetrahydrofuran (10 ml) and the polymer was isolated by pouring the solution into rapidly stirring methanol (500 ml). The fine white powder was then filtered and washed with excess methanol prior to drying to constant weight under vacuum at 60° C.

The dried, white α-methylstyrene polymer was found to weigh 13.88 g. The molecular weight (relative to polystyrene standards) was measured using GPC methods and found to be: $M_w$ 14,300, $M_n$ 4,100 and polydispersity 3.53.

EXAMPLE 12

To a septum sealed 20 ml glass serum bottle, equipped with a magnetic stir bar were added degassed α-methylstyrene (9.82 g, 83.1 mmol) containing 3.7 ppm water and dry toluene (5.51 g). The concentration of water in the monomer was determined by Karl-Fisher coulombic titration. The bottle containing the monomer solution (65% wt. AMS in toluene) was then immersed in an acetone bath regulated at −15 ° C. prior to addition of initiator. The temperature of the polymerization solution was monitored by use of a disposable thermocouple. Once the monomer solution had reached −15° C., a solution of triphenylmethyl tetrakis(pentafluorophenyl)borate (0.8 mg, 0.87 μmol) dissolved in dichloroethane (0.5 ml) was added. The resulting solution was stirred in an acetone bath maintained at −15° C. for a total of 120 minutes. The resulting polymer solution was diluted with tetrahydrofuran (5 ml) and the polymer was isolated by pouring the solution into rapidly stirring methanol (350 ml). The fine white powder was then filtered and washed with excess methanol prior to drying to constant weight under vacuum at 80° C.

The dried, white α-methylstyrene polymer was found to weigh 1.86 g. The molecular weight (relative to polystyrene standards) was measured using GPC methods and found to be: $M_w$ 6,600, $M_n$ 3,000 and polydispersity 2.21.

EXAMPLE 13

To a septum sealed 50 ml glass serum bottle, equipped with a magnetic stir bar were added degassed α-methylstyrene (10.00 g, 84.6 mmol) containing 12.1 ppm water and dry toluene (4.01 g). The concentration of water in the monomer was determined by Karl-Fisher coulombic titration. The bottle containing the monomer solution was then immersed in an acetone bath regulated at −5° C. prior to addition of initiator. The temperature of the polymerization solution (70% wt. AMS in toluene) was monitored by use of a disposable thermocouple. Once the monomer solution had reached −5° C., a solution of triphenylmethyl tetrakis(pentafluorophenyl)borate (1.7 mg, 1.8 µmol) dissolved in dichloroethane (0.5 ml) was added. After an initial exotherm had been observed, the resulting solution was stirred in an acetone bath maintained at −5° C. until the temperature of the polymer solution had decreased to −5° C. The resulting polymer solution was diluted with tetrahydrofuran (5 ml) and the polymer was then isolated by pouring the toluene solution into rapidly stirring methanol (350 ml). The fine white powder was then filtered and washed with excess methanol prior to drying to constant weight under vacuum at 80° C.

The dried, white α-methylstyrene polymer was found to weigh 3.81 g. The molecular weight (relative to polystyrene standards) was measured using GPC methods and found to be: $M_w$ 14,200, $M_n$ 3,600 and polydispersity 3.94.

EXAMPLE 14

To a septum sealed 50 ml glass serum bottle, equipped with a magnetic stir bar were added degassed α-methylstyrene (15.04 g, 127 mmol) containing 5.3 ppm water and dry toluene (22.25 g). The concentration of water in the monomer was determined by Karl-Fisher coulombic titration. Thereafter, 0.58 ml of a 1.00 mg/ml solution containing triphenylmethyltetrakis(pentafluorophenyl) borate in dichloroethane (0.63 µmol) was added. The polymerization solution (40 wt. % AMS in toluene) was stirred at ambient temperature (22° C.) for 30 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 4.96 g. The molecular weight (relative to polystyrene standards) was measured using GPC methods and found to be: $M_w$ 1,400, $M_n$ 670 and polydispersity 1.99.

EXAMPLE 15

To a septum sealed 50 ml glass serum bottle, equipped with a magnetic stir bar were added degassed α-methylstyrene (14.94 g, 126 mmol) containing 5.3 ppm water and dry toluene (22.50 g). The concentration of water in the monomer was determined by Karl-Fisher coulombic titration. Thereafter 0.24 ml of a 1.00 mg/ml solution containing triphenylmethyltetrakis(pentafluorophenyl) borate in dichloroethane (0.26 µmol) was added. The polymerization solution (40 wt. % AMS in toluene) was stirred at ambient temperature (22° C.) for 30 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 1.18 g. The molecular weight (relative to polystyrene standards) was measured using GPC methods and found to be: $M_w$ 3,300, $M_n$ 1,700 and polydispersity 1.92.

EXAMPLE 16

To a septum sealed 50 ml glass serum bottle, equipped with a magnetic stir bar were added degassed α-methylstyrene (15.08 g, 128 mmol) containing 5.3 ppm water and dry toluene (22.37 g). The concentration of water in the monomer was determined by Karl-Fisher coulombic titration. Thereafter 0.16 ml of a 1.00 mg/ml solution containing triphenylmethyltetrakis(pentafluorophenyl) borate in dichloroethane (0.17 µmol) was added. The polymerization solution (40 wt. % AMS in toluene) was stirred at ambient temperature (22° C.) for 30 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 0.89 g. The molecular weight (relative to polystyrene standards) was measured using GPC methods and found to be: $M_w$ 3,600, $M_n$ 1,800 and polydispersity 1.97.

EXAMPLE 17

To a septum sealed 50 ml glass serum bottle, equipped with a magnetic stir bar were added degassed α-methylstyrene (15.00 g, 127 mmol) containing 5.3 ppm water and dry toluene (22.47 g). The concentration of water in the monomer was determined by Karl-Fisher coulombic titration. Thereafter 0.12 ml of a 1.00 mg/ml solution containing triphenylmethyltetrakis(pentafluorophenyl) borate in dichloroethane (0.13 µmol) was added. The polymerization solution (40 wt. % AMS in toluene) was stirred at ambient temperature (22° C.) for 30 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 0.23 g. The molecular weight (relative to polystyrene standards) was measured using GPC methods and found to be: $M_w$ 3,800, $M_n$ 1,900 and polydispersity 2.03.

EXAMPLE 18

To a septum sealed 100 ml glass serum bottle, equipped with a magnetic stir bar were added degassed α-methylstyrene (11.07 g, 93.7 mmol) containing 13.7 ppm water and anhydrous cyclohexane (50.91 g). The concentration of water in the monomer was determined by Karl-Fisher coulombic titration. The bottle containing the monomer solution (20 wt. % in cyclohexane) was then immersed in an ice water bath at 0° C. prior to addition of initiator. The temperature of the polymerization solution was monitored by use of a disposable thermocouple. Once the rapidly stirring monomer solution had reached 0° C., triphenylmethyltetrakis(pentafluorophenyl)borate in dichloroethane (0.28 ml of a 2.73 mg/ml stock solution, 0.83 µmol) was added. The polymerization mixture was stirred at 0° C. for 120 minutes. The resulting polymer that had formed was then isolated by pouring the cyclohexane solution into rapidly stirring methanol (500 ml). The fine, white powder was then filtered and washed with excess methanol. The fine white powder was then washed with excess methanol prior to drying under vacuum at 80° C.

The dried, white α-methylstyrene polymer was found to weigh 10.22 g. The molecular weight (relative to polystyrene standards) was measured using GPC methods and found to be: $M_w$ 3,300, $M_n$ 650 and polydispersity 5.06.

EXAMPLE 19

To a septum sealed 50 ml glass serum bottle, equipped with a magnetic stir bar were added degassed α-methylstyrene (5.03 g, 42.6 mmol) containing 13.7 ppm water and dry hexane (20.55 g). The concentration of water in the monomer was determined by Karl-Fisher coulombic titration. The bottle containing the monomer solution (20 wt % in hexane) was then immersed in an ice water bath at 0° C. prior to addition of initiator. The temperature of the polymerization solution was monitored by use of a disposable thermocouple. Once the rapidly stirring monomer solution had reached 0° C., triphenylmethyltetrakis (pentafluorophenyl)borate in dichloroethane (0.14 ml of a 2.73 mg/ml stock solution, 0.41 μmol) was added. The polymerization mixture was stirred at 0° C. for 120 minutes. The resulting polymer that had precipitated was then collected by filtration and washed with excess methanol. The fine, white powder was then washed with excess methanol prior to drying under vacuum at 80° C.

The dried α-methylstyrene polymer was found to weigh 2.52 g. The molecular weight (relative to polystyrene standards) was measured using GPC methods and found to be: $M_w$ 5,600, $M_n$ 1,800 and polydispersity 3.10.

EXAMPLE 20

To a septum sealed 50 ml glass serum bottle, equipped with a magnetic stir bar were added degassed α-methylstyrene (5.31 g, 44.9 mmol) containing 13.7 ppm water and dry hexane (20.62 g). The concentration of water in the monomer was determined by Karl-Fisher coulombic titration. The bottle containing the monomer solution (20 wt. % in hexane) was then immersed in an ice water bath at 0° C. prior to addition of initiator. The temperature of the polymerization solution was monitored by use of a disposable thermocouple. Once the rapidly stirring monomer solution had reached 0° C., triphenylmethyltetrakis (pentafluorophenyl)borate in dichloroethane (0.08 ml of a 2.73 mg/ml stock solution, 0.24 μmol) was added. The polymerization mixture was stirred at 0° C. for 120 minutes. The resulting polymer that had precipitated was then collected by filtration and washed with excess methanol. The fine, white powder was then washed with excess methanol prior to drying under vacuum at 80° C.

The dried α-methylstyrene polymer was found to weigh 2.54 g. The molecular weight (relative to polystyrene standards) was measured using GPC methods and found to be: $M_w$ 9,000, $M_n$ 3,100 and polydispersity 2.93.

Comparative Example 1

To a septum sealed 50 ml glass serum bottle, equipped with a magnetic stir bar were added degassed α-methylstyrene (10.04 g, 85.0 mmol) containing 3.0 ppm water and dry toluene (5.02 g). The concentration of water in the monomer was determined by Karl-Fisher coulombic titration. The bottle containing the monomer solution was then immersed in an acetone bath regulated at −35° C. prior to addition of initiator. The temperature of the polymerization solution was monitored by use of a disposable thermocouple. Once the monomer solution had reached −35° C., a solution of triphenylmethyl tetrakis(pentafluorophenyl) borate (1.6 mg, 1.7 μmol) dissolved in dichloroethane (0.5 ml) was added. After an initial exotherm had been observed, the resulting solution was stirred in an acetone bath maintained at −35° C. until the temperature of the polymer solution had decreased to −35° C. The resulting polymer solution was diluted with tetrahydrofuran (5 ml) and the resulting polymer was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 8.81 g. The molecular weight (relative to polystyrene standards) was measured using GPC methods and found to be: $M_w$ 57,700, $M_n$ 10,200 and polydispersity 5.64.

Comparative Example 2

To a septum sealed 50 ml glass serum bottle, equipped with a magnetic stir bar were added degassed α-methylstyrene (10.19 g, 86.2 mmol) containing 12.1 ppm water and dry toluene (4.13 g). The concentration of water in the monomer was determined by Karl-Fisher coulombic titration. The bottle containing the monomer solution was then immersed in an acetone bath regulated at −35° C. prior to addition of initiator. Thereafter, a solution of triphenylmethyl tetrakis(pentafluorophenyl)borate (1.6 mg, 1.7 μmol) dissolved in dichloroethane (0.5 ml) was added. The resulting solution was stirred in an acetone bath maintained at −35° C. for 60 minutes. The resulting polymer solution was diluted with tetrahydrofuran (5 ml) and the polymer was then isolated by pouring the toluene solution into rapidly stirring methanol (350 ml). The fine white powder was then filtered and washed with excess methanol prior to drying to constant weight under vacuum at 80° C.

The dried, white α-methylstyrene polymer was found to weigh 9.89 g. The molecular weight (relative to polystyrene standards) was measured using GPC methods and found to be: $M_w$ 51,300, $M_n$ 9,800 and polydispersity 5.24.

Comparative Example 3

To a septum sealed 50 ml glass serum bottle, equipped with a magnetic stir bar were added degassed α-methylstyrene (9.84 g, 83.3 mmol) containing 12.1 ppm water and dry toluene (3.89 g). The concentration of water in the monomer was determined by Karl-Fisher coulombic titration. The bottle containing the monomer solution was then immersed in an acetone bath regulated at −25° C. prior to addition of initiator. The temperature of the polymerization solution was monitored by use of a disposable thermocouple. Once the monomer solution had reached −25° C., a solution of triphenylmethyl tetrakis(pentafluorophenyl) borate (1.5 mg, 1.6 μmol) dissolved in dichloroethane (0.5 ml) was added. After an initial exotherm had been observed, the resulting solution was stirred in an acetone bath maintained at −25° C. until the temperature of the polymer solution had decreased to −25° C. The resulting polymer solution was diluted with tetrahydrofuran (5 ml) and the polymer was then isolated by pouring the toluene solution into rapidly stirring methanol (350 ml). The fine white powder was then filtered and washed with excess methanol prior to drying to constant weight under vacuum at 80° C.

The dried, white α-methylstyrene polymer was found to weigh 8.98 g. The molecular weight (relative to polystyrene standards) was measured using GPC methods and found to be: $M_w$ 34,600, $M_n$ 7,400 and polydispersity 4.66.

Comparative Example 4

To a septum sealed 100 ml glass serum bottle, equipped with a magnetic stir bar were added degassed α-methylstyrene (10.24 g, 86.7 mmol) containing 4.9 ppm water and dry toluene (41.36 g). The concentration of water in the monomer was determined by Karl-Fisher coulombic titration. The bottle containing the monomer solution was then immersed in an acetone bath regulated at −20° C. prior to addition of initiator. The temperature of the polymerization solution was monitored by use of a disposable thermocouple. Once the monomer solution had reached −20° C., a solution of triphenylmethyl tetrakis(pentafluorophenyl) borate (0.3 mg, 0.33 μmol) dissolved in dichloroethane (0.5 ml) was added. The polymerization mixture was stirred while maintained at −20° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 3.22 g. The molecular weight (relative to polystyrene standards) was measured using GPC methods and found to be: $M_w$ 23,700, $M_n$ 7,400 and polydispersity 3.19.

Comparative Example 5

To a septum sealed 50 ml glass serum bottle, equipped with a magnetic stir bar were added degassed α-methylstyrene (5.03 g, 42.6 mmol) containing 4.9 ppm water and dry toluene (22.81 g). The concentration of water in the monomer was determined by Karl-Fisher coulombic titration. The bottle containing the monomer solution was then immersed in an acetone bath regulated at −55° C. prior to addition of initiator. The temperature of the polymerization solution was monitored by use of a disposable thermocouple. Once the monomer solution had reached −55° C., a solution of triphenylmethyl tetrakis(pentafluorophenyl) borate (0.8 mg, 0.87 μmol) dissolved in dichloroethane (0.5 ml) was added. The polymerization mixture was stirred while maintained at −55° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 1.86 g. The molecular weight (relative to polystyrene standards) was measured using GPC methods and found to be: $M_w$ 150,500, $M_n$ 33,600 and polydispersity 4.47.

Comparative Example 6

To a septum sealed 50 ml glass serum bottle, equipped with a magnetic stir bar were added degassed α-methylstyrene (5.74 g, 48.6 mmol) containing 4.9 ppm water and dry toluene (8.63 g). The concentration of water in the monomer was determined by Karl-Fisher coulombic titration. The bottle containing the monomer solution was then immersed in an acetone bath regulated at −20° C. prior to addition of initiator. The temperature of the polymerization solution was monitored by use of a disposable thermocouple. Once the monomer solution had reached −20° C., a solution of triphenylmethyl tetrakis(pentafluorophenyl) borate (1.0 mg, 1.08 μmol) dissolved in dichloroethane (0.5 ml) was added. The polymerization mixture was stirred while maintained at −20° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 5.65 g. The molecular weight (relative to polystyrene standards) was measured using GPC methods and found to be: $M_w$ 31,700, $M_n$ 7,500 and polydispersity 4.22.

Comparative Example 7

To a septum sealed 50 ml glass serum bottle, equipped with a magnetic stir bar were added degassed α-methylstyrene (5.36 g, 45.3 mmol) containing 4.9 ppm water and dry toluene (12.63 g). The concentration of water in the monomer was determined by Karl-Fisher coulombic titration. The bottle containing the monomer solution was then immersed in an acetone bath regulated at −40° C. prior to addition of initiator. The temperature of the polymerization solution was monitored by use of a disposable thermocouple. Once the monomer solution had reached −40° C., a solution of triphenylmethyl tetrakis(pentafluorophenyl) borate (0.4 mg, 0.43 μmol) dissolved in dichloroethane (0.5 ml) was added. The polymerization mixture was stirred while maintained at −40° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 5.06 g. The molecular weight (relative to polystyrene standards) was measured using GPC methods and found to be: $M_w$ 152,200, $M_n$ 44,500 and polydispersity 3.42.

Comparative Example 8

To a septum sealed 50 ml glass serum bottle, equipped with a magnetic stir bar were added degassed α-methylstyrene (5.41 g, 45.8 mmol) containing 4.9 ppm water and dry toluene (12.58 g). The concentration of water in the monomer was determined by Karl-Fisher coulombic titration. The bottle containing the monomer solution was then immersed in an acetone bath regulated at −40° C. prior to addition of initiator. The temperature of the polymerization solution was monitored by use of a disposable thermocouple. Once the monomer solution had reached −40° C., a solution of triphenylmethyl tetrakis(pentafluorophenyl) borate (0.4 mg, 0.43 μmol) dissolved in dichloroethane (0.5 ml) was added. The polymerization mixture was stirred while maintained at −40° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 3.95 g. The molecular weight (relative to polystyrene standards) was measured using GPC methods and found to be: $M_w$ 162,600, $M_n$ 72,300 and polydispersity 2.25.

Comparative Example 9

To a septum sealed 100 ml glass serum bottle, equipped with a magnetic stir bar were added degassed α-methylstyrene (16.08 g, 136 mmol) and toluene (39.91 g). The dry total monomer solution contained 6.0 ppm water as determined by Karl-Fisher coulombic titration. The bottle containing the monomer solution was then immersed in an acetone bath regulated at −35° C. prior to addition of initiator. The temperature of the polymerization solution was monitored by use of a disposable thermocouple. Once the monomer solution had reached −35° C., a solution of triphenylmethyl tetrakis(pentafluorophenyl)borate (1.0 mg, 1.08 μmol) dissolved in dichloroethane (0.5 ml) was added. The polymerization mixture was stirred while maintained at −20° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 0.71 g. The molecular weight (relative to polystyrene standards) was measured using GPC methods and found to be: $M_w$ 136,500, $M_n$ 58,100 and polydispersity 2.35.

Comparative Example 10

To a septum sealed 50 ml glass serum bottle, equipped with a magnetic stir bar were added degassed α-methylstyrene (10.31 g, 87.2 mmol) containing 7.0 ppm water and dry toluene (15.51 g). The concentration of water in the monomer was determined by Karl-Fisher coulombic titration. The bottle containing the monomer solution was then immersed in an acetone bath regulated at −45° C. prior to addition of initiator. The temperature of the polymerization solution was monitored by use of a disposable thermocouple. Once the monomer solution had reached −45° C., triphenylmethyl tetrakis(pentafluorophenyl)borate in dichloroethane (0.40 ml of a 0.98 mg/ml stock solution, 0.42 μmol) was added. The polymerization mixture was stirred at −45° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 1.34 g. The molecular weight (relative to polystyrene standards) was measured using GPC methods and found to be: $M_w$ 188,600, $M_n$ 77,300 and polydispersity 2.44.

Comparative Example 11

To a septum sealed 50 ml glass serum bottle, equipped with a magnetic stir bar were added degassed α-methylstyrene (10.36 g, 87.7 mmol) containing 4.9 ppm water and dry toluene (15.94 g). The concentration of water in the monomer was determined by Karl-Fisher coulombic titration. The bottle containing the monomer solution was then immersed in an acetone bath regulated at −55° C. prior to addition of initiator. The temperature of the polymerization solution was monitored by use of a disposable thermocouple. Once the monomer solution had reached −55° C., a solution of triphenylmethyl tetrakis(pentafluorophenyl) borate (0.4 mg, 0.43 μmol) dissolved in dichloroethane (0.5 ml) was added. The polymerization mixture was stirred while maintained at −55° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 1.50 g. The molecular weight (relative to polystyrene standards) was measured using GPC methods and found to be: $M_w$ 146,100, $M_n$ 49,600 and polydispersity 2.95.

Comparative Example 12

To a septum sealed 50 ml glass serum bottle, equipped with a magnetic stir bar were added degassed α-methylstyrene (9.73 g, 82.3 mmol) containing 7.0 ppm water and dry toluene (14.86 g). The concentration of water in the monomer was determined by Karl-Fisher coulombic titration. The bottle containing the monomer solution was then immersed in an acetone bath regulated at −20° C. prior to addition of initiator. The temperature of the polymerization solution (40 wt. % AMS in toluene) was monitored by use of a disposable thermocouple. Once the monomer solution had reached −20° C., triphenylmethyl tetrakis (pentafluorophenyl)borate in dichloroethane (1.55 ml of a 0.98 mg/ml stock solution, 1.65 μmol) was added. The polymerization mixture was stirred at −40° C. for 120 minutes. The resulting polymer that had formed was then isolated by pouring the toluene solution into rapidly stirring methanol (500 ml). The fine white powder was then filtered and washed with excess methanol prior to drying to constant weight under vacuum at 80° C.

The dried, white α-methylstyrene polymer was found to weigh 8.21 g. The molecular weight (relative to polystyrene standards) was measured using GPC methods and found to be: $M_w$ 23,400, $M_n$ 1,200 and polydispersity 19.32.

What is claimed is:

1. A process for preparing oligomers of α-methylstyrene having a molecular weight of 5000 ($M_n$) and less comprising reacting α-methylstyrene with an initiator of the formula [M][WCA] at a temperature of −15° C. to about 35° C., wherein M is lithium or a carbocation of the formula $C^+(R^1)(R^2)(R^3)$ wherein $R^1$, $R^2$, and $R^3$ independently represent substituted and unsubstituted hydrocarbyl radicals, and WCA represents a weakly coordinating borate anion.

2. The process of claim 1 wherein $R^1$, $R^2$ and $R^3$ independently represent hydrogen, substituted and unsubstituted linear and branched ($C_1$ to $C_{20}$) alkyl, ($C_5$ to $C_{10}$) cycloalkyl, ($C_6$ to $C_{14}$) aryl, and ($C_7$ to $C_{24}$) aralkyl, provided that only one of $R^1$, $R^2$, and $R^3$ can represent hydrogen.

3. The process of claim 2 wherein $R^1$, $R^2$, and $R^3$ are independently phenyl, biphenyl, tolyl, and xylyl.

4. A The process of claim 2 wherein $R^1$, $R^2$, and $R^3$ are each phenyl.

5. The process of claim 1 wherein said weakly coordinating borate anion is represented by the formula:

wherein each of $R^4$ independently represents a substituted aryl radical wherein at least two of said substituents are selected from the group consisting of fluorine, linear and branched $C_1$ to $C_{20}$ fluoroalkyl, fluorophenyl, and combinations thereof, $R^5$ is the same as $R^4$ or can represent hydrogen, linear or branched $C_1$ to $C_{20}$ alkyl, linear or branched $C_2$ to $C_{20}$ alkenyl, $C_5$ to $C_{10}$ cycloalkyl, $C_6$ to $C_{14}$ aryl, and $C_7$ to $C_{24}$ aralkyl.

6. The process of claim 5 wherein said borate anion is selected from the group consisting of tetrakis (pentafluorophenyl)borate, tetrakis(3,5-bis(trifluoromethyl) phenylborate, tetrakis(3,5-difluorophenyl)borate, tetrakis(2, 3,4,5-tetrafluorophenyl)borate, tetrakis(3,4,5,6-tetrafluorophenyl)borate, tetrakis(3,4,5-trifluorophenyl) borate, methyltris(perfluorophenyl)borate, ethyltris (perfluorophenyl)borate, phenyltris(perfluorophenyl)borate, and tetrakis(perfluorobiphenyl)borate.

7. The process of claim 1 wherein said initiator is selected from the group consisting of lithium tetrakis (perfluorophenyl)borate and trityl tetrakis(perfluorophenyl) borate.

8. The process of claim 1 wherein said temperature ranges form about 0° C. to about 30° C.

9. The process of claim 8 wherein said temperature ranges from about 5° C. to about 25° C.

10. The process of claim 1 wherein the ratio of α-methylstyrene monomer to single component initiator ranges from about 2000:1 to about 1,000,000:1 (mole to mole basis).

11. The process of claim 10 wherein the ratio of α-methylstyrene monomer to single component initiator ranges from about 10,000:1 to about 20,000:1 (mole to mole basis).

12. The process of claim 1 wherein α-methylstyrene is reacted with said initiator in the presence of a hydrocarbon or aromatic diluent.

13. The process of claim 12 wherein said diluent is selected from benzene, toluene, xylenes, cumene, propane, butane, pentane, hexane, and cyclohexane.

14. The process of claim 12 wherein diluent is a non-solvent for poly(α-methylstyrene).

15. The process of claim 14 wherein said diluent is selected from a linear or branched $C_3$ to $C_6$ alkane.

16. The process of claim 1 wherein said reaction is conducted in bulk.

17. process for preparing oligomers of α-methylstyrene having a molecular weight ranging from about 500 to about 5000 ($M_n$) comprising reacting α-methylstyrene monomer with an initiator selected from the group consisting of a lithium or carbocation salt of a orate anion selected from the group consisting of tetrakis(pentafluorophenyl)borate, tetrakis(3,5-bis(trifluoromethyl)phenylborate, tetrakis(3,5-difluorophenyl)borate, tetrakis(2,3,4,5-tetrafluorophenyl) borate, tetrakis(3,4,5,6-tetrafluorophenyl)borate, tetrakis(3,4,5-trifluorophenyl)borate, methyltris(perfluorophenyl) borate, ethyltris(perfluorophenyl)borate, phenyltris (perfluorophenyl)borate, and tetrakis(perfluorobiphenyl) borate, at a temperature range of about −15° C. to about 35° C.

18. The process of claim 17 wherein said carbocation is represented by the formula $C^+(R^1)(R^2)(R^3)$, wherein $R^1$, $R^2$, and $R^3$ independently represent substituted and unsubstituted hydrocarbyl radicals.

19. The process of claim 18 wherein $R^1$, $R^2$ and $R^3$ independently represent hydrogen, substituted and unsubstituted linear and branched ($C_1$ to $C_{20}$) alkyl, ($C_5$ to $C_{10}$) cycloalkyl, ($C_6$ to $C_{14}$) aryl, and ($C_7$ to $C_{24}$) aralkyl, provided that only one of $R^1$, $R^2$, and $R^3$ can represent hydrogen.

20. The process of claim 19 wherein $R^1$, $R^2$, and $R^3$ are independently phenyl, biphenyl, tolyl, and xylyl.

21. The process of claim 20 wherein said carbocation is triphenylcarbenium.

22. The process of claim 21 wherein said initiator is selected from the group consisting of lithium tetrakis (perfluorophenyl)borate and trityl tetrakis(perfluorophenyl) borate.

23. The process of claim 22 wherein said reaction is conducted in a diluent selected from the group consisting of a hydrocarbon and aromatic diluent.

24. The process of claim 23 wherein said diluent is selected from the group consisting of benzene, toluene, xylenes, cumene, propane, butane, pentane, hexane, and cyclohexane.

25. The process of claim 23 wherein diluent is a non-solvent for poly(α-methylstyrene).

26. The process of claim 25 wherein said diluent is selected from the group consisting of a linear or branched $C_3$ to $C_6$ alkane.

27. The process of claim 17 wherein said reaction is conducted in bulk.

* * * * *